United States Patent
Delmas et al.

(10) Patent No.: US 7,534,036 B2
(45) Date of Patent: May 19, 2009

(54) METHOD AND ARRANGEMENT FOR A MOBILE IMAGING SYSTEM

(75) Inventors: Yann Delmas, Meudon (FR); Bernard Bouvier, Eragny sur Oise (FR); Andreas C. Van der Ham, Nieuwegein (NL)

(73) Assignee: General Electric Company, Schenectady, NY (US)

( * ) Notice: Subject to any disclaimer, the term of this patent is extended or adjusted under 35 U.S.C. 154(b) by 48 days.

(21) Appl. No.: 11/552,822

(22) Filed: Oct. 25, 2006

(65) Prior Publication Data

US 2008/0101546 A1 May 1, 2008

(51) Int. Cl.
*H05G 1/02* (2006.01)
(52) U.S. Cl. .................... 378/196; 378/197; 378/198
(58) Field of Classification Search .......... 378/196–198
See application file for complete search history.

(56) References Cited

U.S. PATENT DOCUMENTS

| | | | | |
|---|---|---|---|---|
| 3,281,598 A | * | 10/1966 | Hollstein | 378/179 |
| 4,412,346 A | * | 10/1983 | Takenouti et al. | 378/181 |
| 5,038,371 A | * | 8/1991 | Janssen et al. | 378/197 |
| 5,073,917 A | * | 12/1991 | Van Endschot et al. | 378/197 |
| 5,291,540 A | * | 3/1994 | Futamata | 378/197 |
| 5,521,957 A | * | 5/1996 | Hansen | 378/198 |
| 5,617,462 A | * | 4/1997 | Spratt | 378/98.7 |
| 6,264,364 B1 | | 7/2001 | Pflaum et al. | |
| 6,434,751 B1 | | 8/2002 | Gustafson | |
| 6,461,039 B1 | * | 10/2002 | Klotz et al. | 378/197 |
| 6,582,120 B2 | * | 6/2003 | Schomberg | 378/197 |
| 6,619,840 B2 | * | 9/2003 | Rasche et al. | 378/197 |
| 6,742,929 B2 | * | 6/2004 | Horbaschek | 378/197 |
| 7,018,097 B2 | | 3/2006 | Schmitt | |
| 2002/0118793 A1 | | 8/2002 | Horbaschek | |
| 2004/0008820 A1 | | 1/2004 | Schmitt | |

FOREIGN PATENT DOCUMENTS

DE 8905588 9/1990

* cited by examiner

*Primary Examiner*—Edward J Glick
*Assistant Examiner*—Thomas R Artman

(57) ABSTRACT

A support assembly for an image detector operable to acquire an image of a subject on a table is provided. The support assembly includes an offset arm pivotally coupled from a carriage about a first axis. An elbow is pivotally coupled at the offset arm about a second axis. The first and second axes are vertically aligned and spaced an offset distance from one another. A mobile arm supports the image detector. The mobile arm is pivotally coupled at the elbow about a third axis that is horizontal aligned and in alignment with a central longitudinal axis of a table in a vertical plane. The mobile arm is also supported to rotate about a fourth axis that is horizontal aligned and in perpendicular alignment relative to the third axis. The first, second, third, and fourth axes all include a common point of intersection with one another.

11 Claims, 5 Drawing Sheets

METHOD AND ARRANGEMENT FOR A MOBILE IMAGING SYSTEM

BACKGROUND OF THE INVENTION

The subject matter herein relates generally to image acquisition, and more specifically, to a method and arrangement for a mobile imaging machine or system. The mobile imaging machine or system can be configured for medical diagnostic or industrial imaging.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient, for example. The generated images may be used for many purposes. For instance, internal defects in an object may be detected. Additionally, changes in internal structure or alignment may be determined. Fluid flow within an object may also be represented. Furthermore, the image may show the presence or absence of objects in the patient. The information gained from medical diagnostic imaging has applications in many fields, including medicine and manufacturing.

A certain conventional medical diagnostic imaging system includes a mobile C-arm system. The mobile C-arm system may be used for general surgery, vascular procedures, and cardiac procedures, for example. The conventional mobile C-arm system is equipped with a radiological source or transmitter in opposed relation to a radiological detector (e.g., an image intensifier), and is moved in relation to the imaged subject or patient on tabletop. With the patient positioned between the radiological source and detector, the C-arm system is moved and rotated so as to pass radiation through the imaged subject from various directions. As the radiation passes through the patient, anatomical structures cause variable attenuation of the radiation passing through and received at the detector. The detector translates the attenuated radiation into an image employed in diagnostic evaluations. In typical medical procedures around such diagnostic imaging systems, multiple physicians, nurses, and technicians are located in close proximity to the imaged subject.

There is a need for a medical diagnostic imaging system with enhanced mobility that can be readily put in arbitrary positions in a crowded work environment, with reduced interference to the clinicians or patient.

BRIEF DESCRIPTION OF THE INVENTION

The above-mentioned need is addressed by the embodiments described herein in the following description.

In one embodiment, a support assembly in movable support of a radiation source and detector operable in combination to acquire a radiological image of a subject positioned on a table is provided. The table defined by a central longitudinal axis. The support assembly includes an offset arm pivotally coupled from a mobile carriage about a first axis generally vertically aligned. An elbow is pivotally coupled at the offset arm about a second axis. The first and second axes are each generally vertically aligned and spaced an offset distance from one another. A mobile arm is mounted in support of a radiation source and detector. The mobile arm is pivotally coupled at the elbow about a third axis that is generally horizontal aligned and in general alignment with a central longitudinal axis of a table in a vertical plane. The mobile arm is also supported to rotate about a fourth axis that is generally horizontal aligned and in general perpendicular alignment relative to the third axis. The first axis, the second axis, the third axis, and the fourth axis all include a common point of intersection with one another.

In another embodiment, an arrangement operable to acquire a diagnostic image of a subject is provided. The arrangement includes a table to receive the subject to be imaged, a carriage, an offset arm, and an elbow. The table is defined by a central longitudinal axis. The carriage is operable to move relative to the table. The offset arm includes a first end opposite a second end. The first end of the offset arm is pivotally supported at the carriage about a first axis generally vertically aligned. The elbow is pivotally supported at the second end of the offset arm about a second axis generally vertically aligned and spaced an offset distance from the first axis. The arrangement further includes a radiation source configured in communication with a radiation detector to acquire the diagnostic image, and a mobile arm in support of the radiation source and the radiation detector. The mobile arm is pivotally supported from the elbow about a third axis generally horizontally aligned above with the central longitudinal axis of the table in a vertical plane. The mobile arm is also slidably supported to rotate about a fourth axis generally horizontal aligned perpendicular relative to the third axis. The first axis, the third axis, and the fourth axis all include a common point of intersection with another.

In yet another embodiment, a method of communicating radiation from a radiation source through a table to a radiation detector is provided. The method comprises the acts of sliding an carriage in a linear direction along a rail fixed and located above in a vertical direction in relation to the table; pivoting a first end of an offset arm about a first axis with respect to the carriage; pivoting an elbow with respect to the second end of the offset arm about a second axis generally vertically aligned and spaced an offset distance in a horizontal direction from the first axis; pivoting a mobile arm about a third axis in relation to the elbow, the third axis being generally horizontally aligned and generally aligned with a central longitudinal axis of the table in a vertical plane; rotating the mobile arm about a fourth axis in relation to the elbow, the fourth axis generally horizontal aligned and generally perpendicular aligned relative to the third axis; and transmitting radiation from a radiation source at one free end of the mobile arm toward the radiation detector.

Arrangements of varying scope are described herein. In addition to the aspects and advantages described in this summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
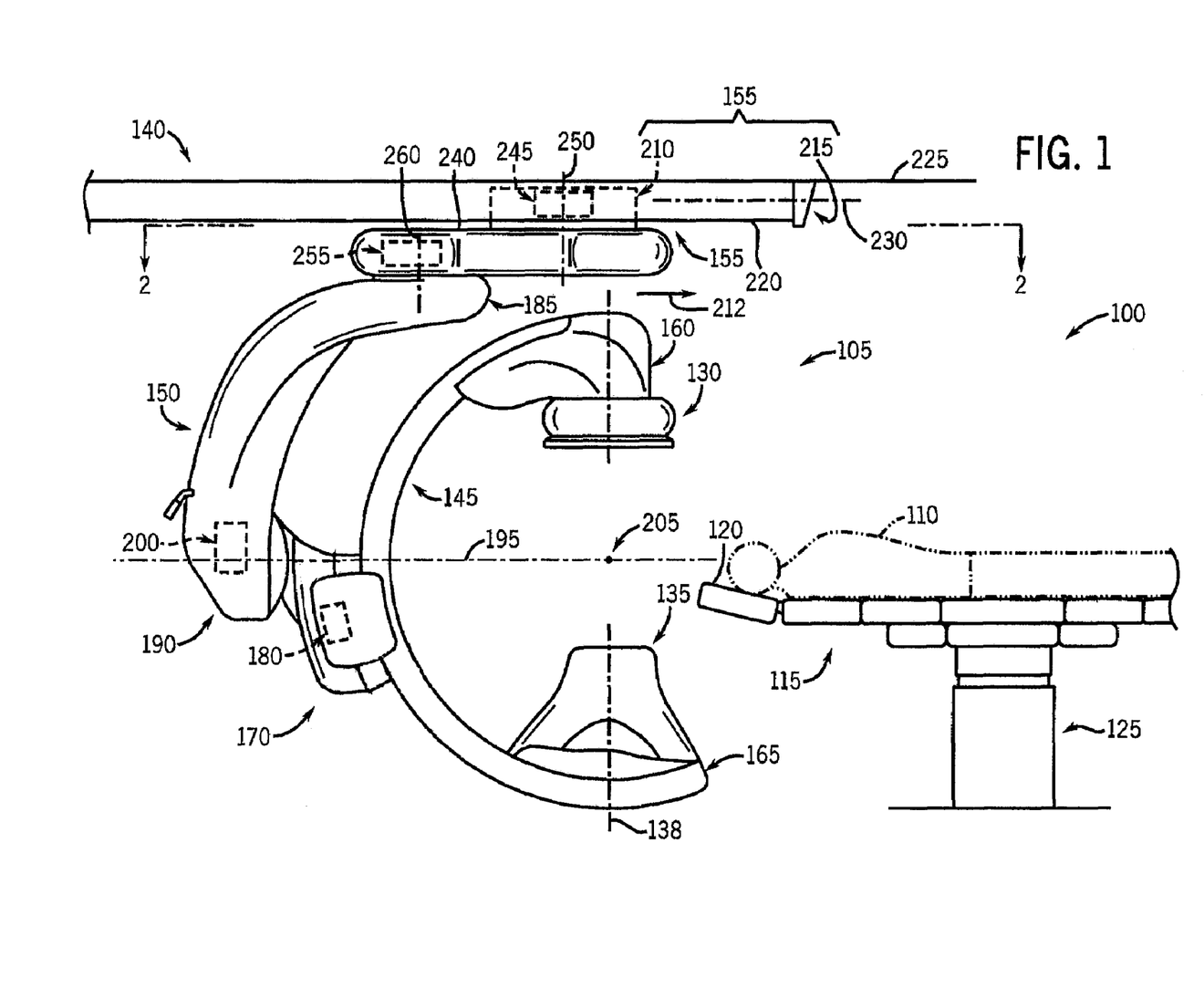
FIG. 1 shows a schematic diagram of an elevation view of an embodiment of an arrangement of an imaging system in combination with a table in support of an imaged subject.

FIG. 1 illustrates an embodiment of an arrangement 100 that comprises an imaging system 105 operable to acquire a radiological image of an imaged subject 110 positioned on a table 115. The imaged subject 110 is typically a patient or some portion of the patient. The imaging system 105 can be operated remotely, for example so that an operator can be shielded from radiation. Alternatively, the imaging system 105 can be placed in an examining or operating room so that a health care provider can view images while performing a medical procedure of the imaged subject 110.

The table 115 generally comprises a tabletop 120 supported from a base 125 independent from the imaging system 105. The tabletop 120 is generally configured to receive the imaged subject 110 along a central longitudinal axis 128 (See FIGS. 2-4). The table 115 can be fixed or moveable. In addition, the table 115 can comprise various conventional advance/withdraw mechanisms, lift mechanisms and/or tilt mechanisms operable to move the tabletop 120 and imaged subject 110 to a desired raised/lowered, tilted, and/or advanced/withdrawn position. Accordingly, the table 115 can be interfaced with the imaging system 105 to communicate control and positioning of the table 115 in relation to the imaging system 105.

Still referring to FIG. 1, the illustrated imaging system 105 is a mobile X-ray imaging system, operable to pass X-rays through a patient and then detect and process a diagnostic image for interpretation. Yet, the type of imaging system 105 (e.g., magnetic resonance imaging, radiological, etc.) can vary. The illustrated imaging system 105 generally includes a radiation source 130 and a radiation detector or receiver 135. The exemplary radiation source 130 generates X-ray photons preferably directed to pass through a collimator and form an x-ray beam. The X-ray beam has an axis 138 that is substantially aligned with the center of the active area of the detector 135. The X-ray beam has a vector that is defined by the axis of the X-ray beam in the direction of the detector 135. Although the illustrated radiation source 130 is operable to generate X-rays, the type of radiation source 130 and respective detector 135 can vary.

The imaging system 105 further includes a support assembly 140 in mobile support of the radiation source 130 and detector 135 in relation to the imaged subject 110 resting on the table 115. The support assembly 140 includes a mobile arm 145, supported by an elbow 150 from a mobile carriage system 155. The illustrated mobile arm 145 is a C-arm having a pair of opposed free ends 160 and 165. The radiation detector 135 is connected at the first free end 160, and the radiation detector 135 is connected at the second free end 165 in opposed so as to receive attenuated radiation passing through the imaged subject 110 located therebetween. Yet, the shape of the mobile arm 145 can be curvilinear, angular, etc. and is not limiting.

Still referring to FIG. 1, a collar or trolley assembly 170 is configured to slidably receive the mobile arm 145 therethrough so as to be rotatable about an axis of rotation 175 (See FIG. 2) aligned generally horizontal and perpendicular to the central longitudinal axis 128 of the tabletop 120. A motorized drive 180 is configured to move the mobile arm 145 about the axis of rotation 175 in sliding relation through the collar assembly 170.

The elbow 150 is connected in pivotal support of the collar assembly 170 and the mobile arm 145. The illustrated elbow 150 is generally L-shaped, and includes an upper free end 185 and lower free end 190. The lower free end 190 of the elbow 150 is connected in rotational support of the collar assembly 170 and mobile arm 145 so as to rotate about an axis of rotation 195. The axis of rotation 195 is aligned generally horizontal and perpendicular to the axis of rotation 175 of the mobile arm 145 about the collar assembly 170. The axis of rotation 195 is also aligned generally parallel to the central longitudinal axis 128 (See FIGS. 2-4) of the tabletop 120. Although the illustrated elbow 150 is L-shaped, the shape of the elbow 150 can vary. A motorized drive 200 is generally operable to rotate the mobile arm 145 and collar assembly 170 about the axis of rotation 195 with respect to the elbow 150. The support assembly 140 is configured such that the axis of rotation 175 intersects the axis of rotation 195 of the mobile arm 145 at a point of intersection 205, herein referred to as the isocenter 205.

As further illustrated in FIG. 1, the mobile carriage system 155 generally includes a carriage 210 operable to move the collar assembly 170 and mobile arm 145 in a linear direction 212 along a rail support structure 215. The illustrated rail support structure 215 includes a pair of parallel-aligned rails 220 fixed to overhead (e.g., to a ceiling 225) and configured to receive the carriage 210 therebetween. The rail support structure 215 generally defines a central longitudinal axis 230 inline with the linear direction of travel 212 of the carriage 210. The central longitudinal axis 230 of the rail support structure 215 is generally located above the axis of rotation 195 of the mobile arm 145 and the central longitudinal axis 128 of the tabletop 120 in the vertical direction. Also, the central longitudinal axis 230 of the rail support structure 215 is aligned such that, in top plan view, there is no offset between the central longitudinal axis 230 of the rail support structure 215, the rotation axis 195 of the mobile arm 145, and the central longitudinal axis 128 of the tabletop 120.

An offset arm 240 is connected in rotationally support of the elbow 150 and mobile arm 145 from the mobile carriage system 155. A motorized swivel drive 245 is connected to rotate the offset arm 240 about a first axis 250 with respect to the carriage 210. An elbow drive 255 is connected to rotate the elbow 150 about a second axis 260 with the respect to the offset arm 240. The first and second axes 250 and 260 are both generally vertically aligned in parallel with one another, as well as spaced or offset a distance from one another in the general horizontal direction in top plan view. A central longitudinal axis 262 of the offset arm 240 is generally linear aligned and extends through the first and second axes 250 and 260.

Figure 2:
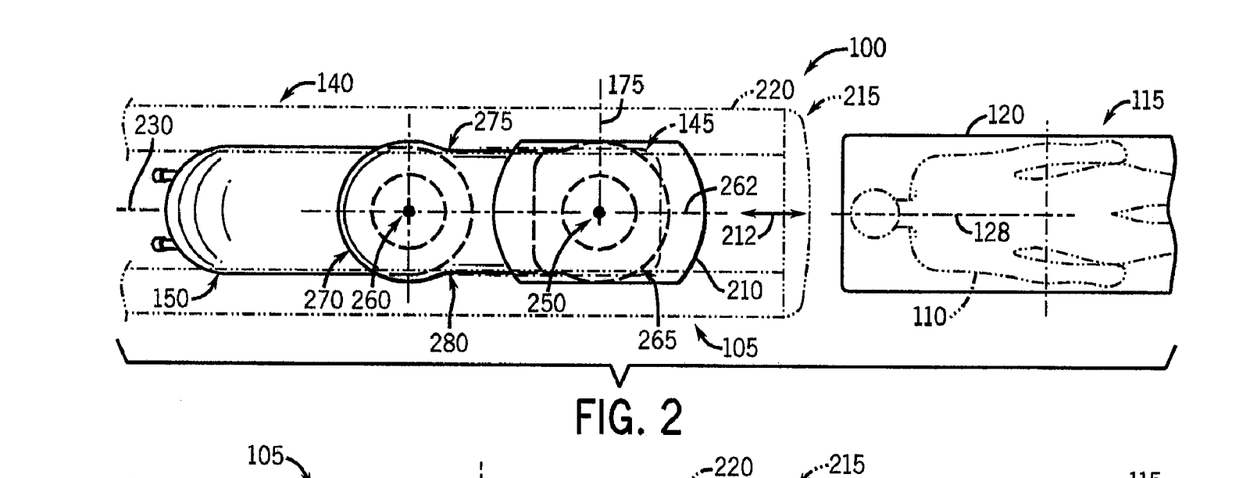
FIG. 2 shows a schematic diagram along line 2-2 in FIG. 1.
Figure 3:
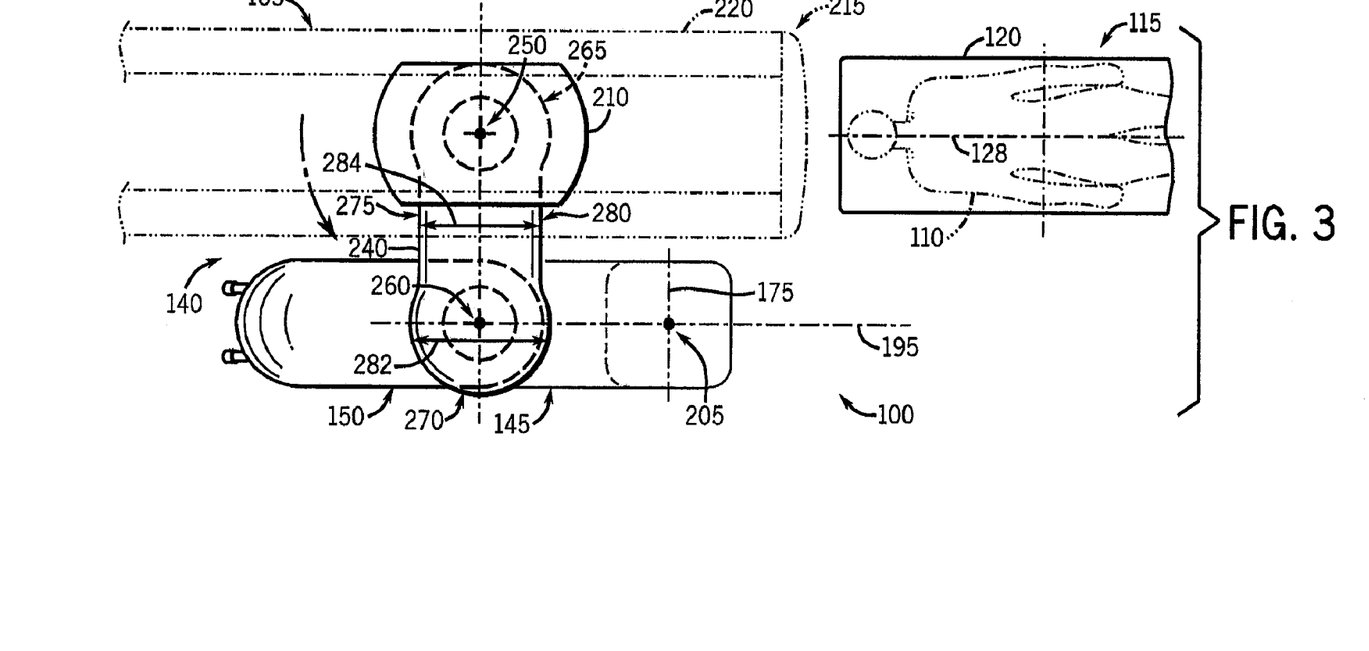
FIG. 3 shows a schematic diagram of a top plan view of the imaging system shown in FIG. 1, a mobile arm aligned laterally offset from the table.

In top plan view as illustrated in FIG. 2, the illustrated offset arm 240 includes opposed, curvilinear-shaped free ends 265 and 270 and a pair of opposing, generally linear-shaped sides extending therebetween 275 and 280. As shown in FIG. 3, a general diameter 282 of the curvilinear-shaped free ends 265 and 270 is greater than a width 284 between the linear shaped sides 275 and 280, creating a generally figure-eight shape. In side elevation view as illustrated in FIG. 1, the circumferential edge free ends 265 and 270 and sides 275 and 280 of the offset arm 240 is rounded or curvilinear-shaped in the general vertical direction. This configuration of the offset arm 240 provides for enhanced maneuverability as well as an aesthetically appealing appearance.

Having generally provided the above-description of a construction of the embodiment the arrangement 100 of the imaging system 105 and the table 115, the following is a general description of the operation of the arrangement 100 in acquiring a medical diagnostic image of a subject 110 positioned on the table 115.

Assume initially that the support assembly 140 of the imaging system 105 is at an exemplary parked or zero position, as illustrated in FIGS. 1 and 2. At this parked position, the central longitudinal axis 230 of the offset arm 240 and the axis of rotation 195 of the mobile arm 145 are both aligned in parallel with the central longitudinal axis 128 of the tabletop 120. The first axis 250 about which the offset arm 240 rotates with respect to the carriage 210 intersects at the isocenter 205 of the support assembly 140. The support assembly 140 is operable to move the mobile arm 145 and mounted radiation source 130 and detector 135 in the linear direction 212 in relation to the central longitudinal axis 128 of the tabletop 120. The swivel drive 245 is operable to rotate the offset arm 240 about the first axis 250 with respect to the carriage 210 in a manner such that the first axis 250 continuously intersects the isocenter 205 of the support assembly 140. Accordingly, as illustrated in top plan view in FIGS. 2 and 4, the mobile arm 145 and mounted radiation source 130 and detector 135 (See FIG. 1) can be rotated around the first axis 250 and/or the rotation axis 195 while maintaining the isocenter 205 (See FIG. 1) at a point of interest on the imaged subject 110.

As illustrated in FIG. 3, the swivel drive 245 (See FIG. 1) is operable to rotate the offset arm 240 about the first axis 250 with respect to the carriage 210, allowing the mobile arm 145 to be positioned laterally offset to the right-hand side of the table 115 and the imaged subject 110. The elbow 150 can also be rotated about the second axis 260 with respect to the offset arm 240 so as to align the rotation axis 195 of the mobile arm 145 in parallel relative to the longitudinal axis 128 of the tabletop 210 in a desired manner. It is apparent from FIG. 3 that the movement of the mobile arm 145 and mounted radiation source 130 and detector 135 (See FIG. 1) to the laterally offset position from the table 115 enhances access for a clinician or physician (e.g., by an anesthesiologist) over the top and at the head of the imaged subject 110 during a medical procedure in a desired manner.

Figure 4:
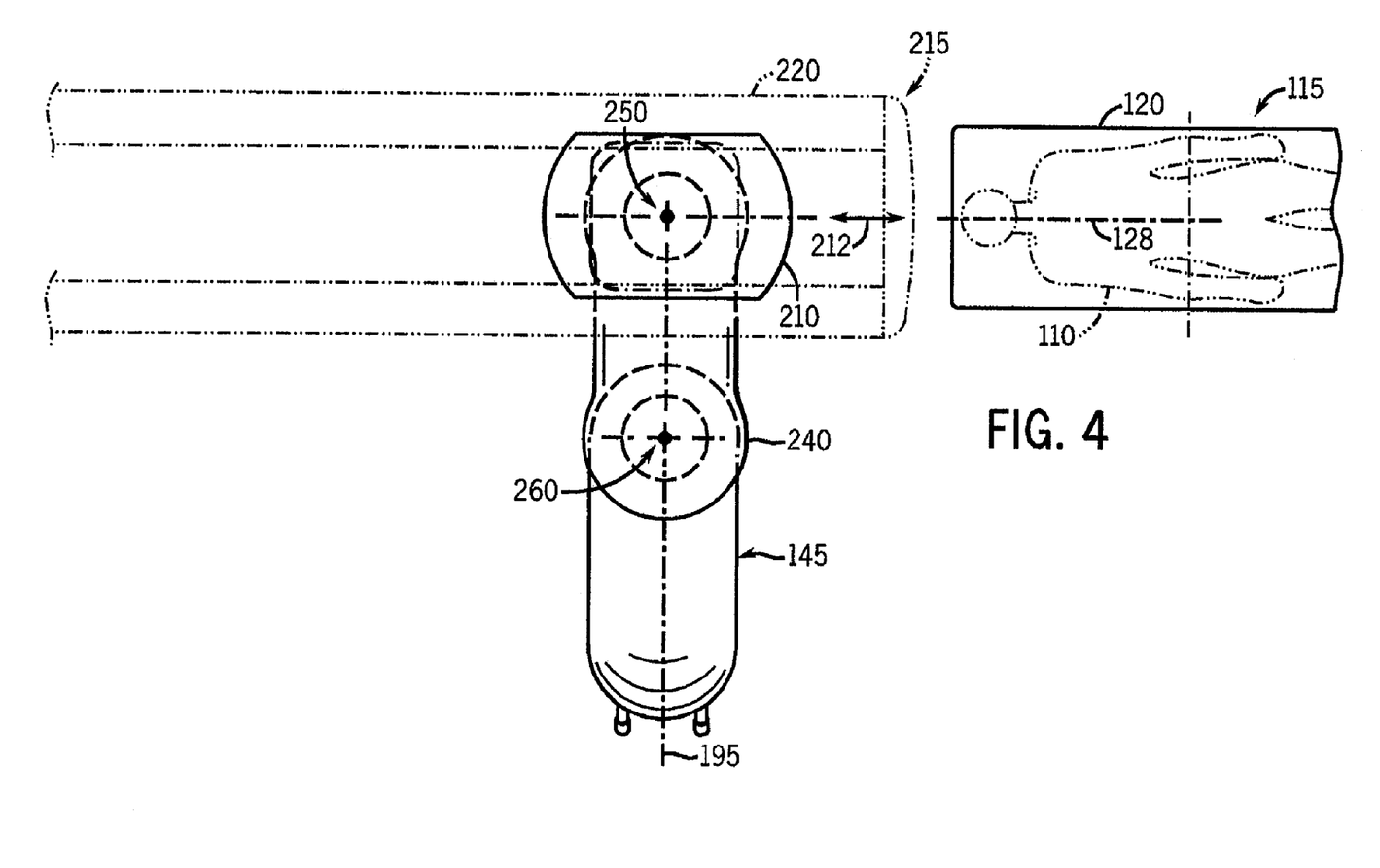
FIG. 4 shows a schematic diagram of a top plan view of the imaging system shown in FIG. 1, a mobile arm aligned orthogonal to the table.

FIG. 4 illustrates a top plan view of the mobile arm 145 rotated by the elbow drive about the first axis 250 to a generally perpendicular alignment of the rotation axis 195 with the central longitudinal axis 128 of the tabletop 120. With this rotation of the mobile arm 145, the axis 138 (See FIG. 1) extending between the radiation source 130 and detector 135 (See FIG. 1) maintains vertical alignment with the first axis 250. With movement of mobile arm 145 in the linear direction 212, the radiation source 130 and detector 135 are operable to capture radiological images of the subject 110 from head-to-toe, while allowing a clinician or physician access at the head of the imaged subject 110. In a reverse manner, the imaging system 105 can be readily returned to the parked position illustrated in FIGS. 1 and 2.

Although FIGS. 3 and 4 illustrate movement of the mobile arm 145 laterally offset to the right-hand side of the tabletop 120 of the table 115 and imaged subject 110, it should be understood that the mobile arm 145 can be moved to an opposite laterally offset position at the left-hand side of the tabletop 210 and imaged subject 110 in a similar manner.

Figures 5, 6:
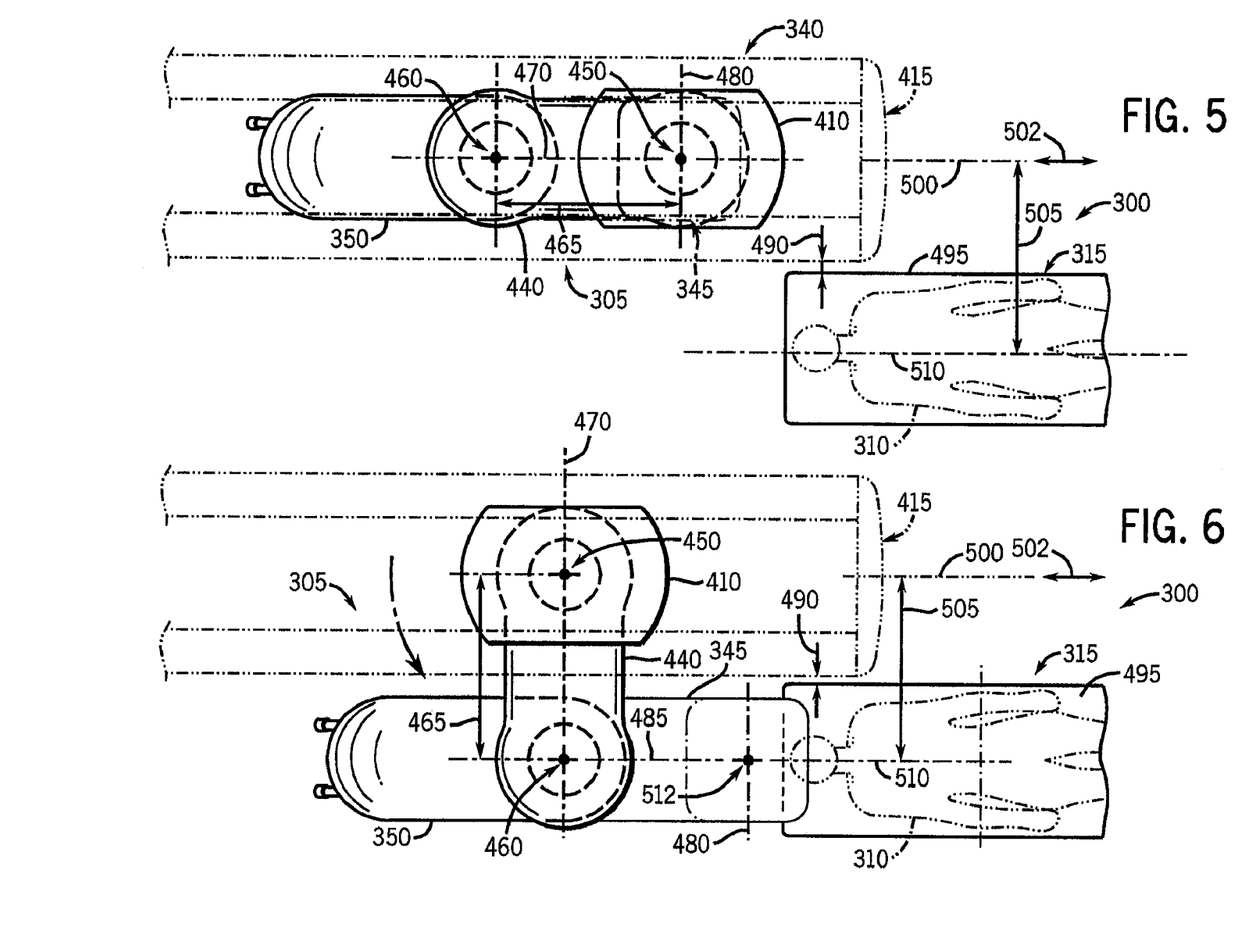
FIG. 5 illustrates a schematic diagram of a top plan view of another embodiment of an imaging system in relation to a table in support of an imaged subject.
FIG. 6 illustrates a schematic diagram of a top plan view of the imaging system shown in FIG. 5, a mobile arm co-aligned with the table.
Figure 7:
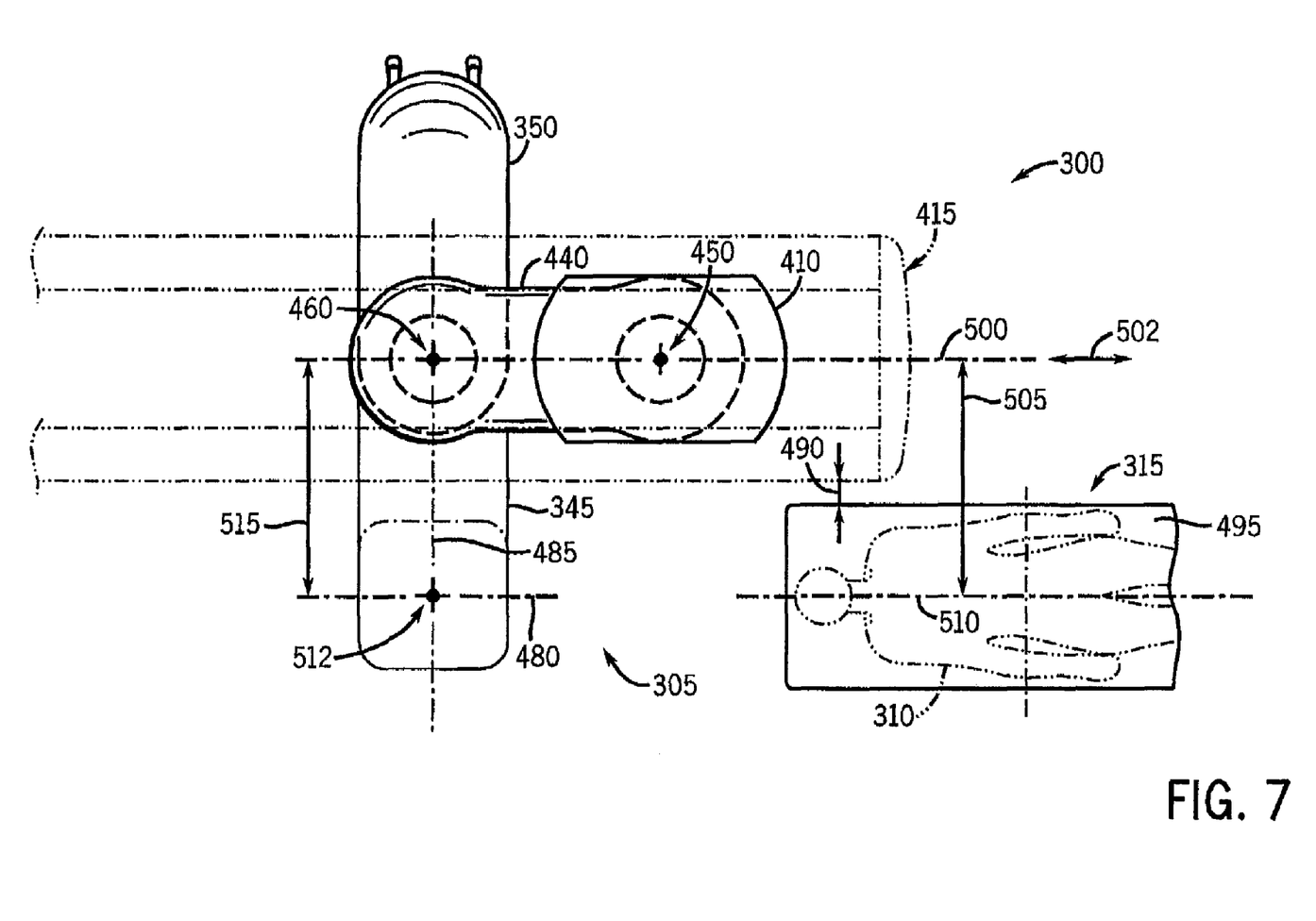
FIG. 7 illustrates a schematic diagram of a top plan view of the imaging system shown in FIG. 5, a mobile arm aligned orthogonal to the table.

FIG. 5-7 illustrate another embodiment of an arrangement 300 that comprises imaging system 305 operable to capture a diagnostic image of a subject 310 on a table 315, similar to the arrangement 100 described above. Referring specifically to FIG. 5, the imaging system 305 includes a support assembly 340 having a mobile arm 345 supported by an elbow 350 from a carriage 410 movable along a ceiling mounted rail support structure 415, and an offset arm 440, similar in construction and operation to the mobile arm 145, the elbow 150, the rail support structure 215, and the offset arm 240 of support assembly 140 described above. The offset arm 440 is connected to rotate about a first axis 450 with respect to the carriage 410, and the elbow 350 is connected to rotate about a second axis 460 with respect to the offset arm 440. The first and second axes 450 and 460 are each generally vertically aligned, spaced a distance (illustrated by arrow and reference 465) apart, and generally define a central longitudinal axis 470 of the offset arm 440 therethrough.

Still referring to FIG. 5, the rail support structure 415 of the support assembly 340 is spaced a clearance distance 490 from a tabletop 495 of the table 315 in the horizontal direction in top plan view. Accordingly, no part of the support assembly 340, including the mobile arm, 345, the elbow 350, the rail support structure 415 and the carriage 410 supported thereon, and the offset arm 440, is located over the imaged subject 310 resting on the table 315. This configuration allows a clinician or physician (e.g., anesthesiologist) enhanced access over the head of the imaged subject 310. In addition, the offset location of the rail support structure 415 of the support assembly 340 reduces a likelihood of interference with an ability of a procedural room's lighting system to properly illuminate an area of interest of the imaged subject 310. In further addition, the offset location of the rail support structure 415 of the support assembly 340 reduces a likelihood of interference with a flow of air typically provided over the imaged subject 310 in a conventional manner so as to maintain an elevated pressure zone that enhances a sterile environment over an area of interest of the imaged subject 310.

FIG. 6 is a top plan view illustrating rotation of the offset arm 440 to a generally perpendicular alignment with a central longitudinal axis 500 of the rail support structure 415. At this rotated position, a linear direction of movement (illustrated by arrow and reference 502) of the carriage 410 along the central longitudinal axis 500 of the rail support structure 415 is spaced a distance 505 from a central longitudinal axis 510 of the tabletop 315. The distance 505 is generally equal to the offset distance 465 between generally vertically aligned first and second axes 450 and 460, respectively. Accordingly, when the central longitudinal axis 470 of the offset arm 440 is aligned generally perpendicular to the central longitudinal axis 500 of the rail support structure 315 and the linear direction of movement 502 of the carriage 410, the central longitudinal axis 510 of the tabletop 495 of the table 315 extends through an isocenter 512 of the imaging system 305, and the generally vertical rotation axis 460 of rotation of the elbow 350 about the offset arm 440.

Although FIG. 6 shows the central longitudinal axis 500 of the rail support structure 415 offset in one direction (e.g., left-hand side of subject 310) from the central longitudinal axis 510 of the table 315, it is understood that the central longitudinal axis 500 of the rail structure 415 can also be offset in the opposite direction from the central longitudinal axis 510 of the table 315 and is encompassed herein.

FIG. 7 illustrates a top plan view of the mobile arm 345 rotated with respect to the elbow 350 about the second axis 460. The generally vertically aligned rotation axis 460 of the elbow 350 about the offset arm 440 is spaced a general horizontal distance 515 from the isocenter 512 and the rotation axis 480 of the mobile arm 345 about the collar 170 (See FIG. 1). The generally horizontal distance 515 is about equal to the distance 505 such that the central longitudinal axis 510 of the tabletop 495 is generally aligned with the rotation axis 480 of the mobile arm 345 about the collar 170 (See FIG. 1). Thereby, the arrangement 300 allows movement of the tabletop 495 and/or the carriage 410 in the linear direction 502 in relation to one another so as to readily acquire radiological images from head-to-toe of the imaged subject 310. This above-described subject matter is desired, for example, in following radiological dye through a circulation system of the imaged system 310.

In operation, assume initially that the support assembly 340 is located in a parked or zero position illustrated in FIG. 5 where a generally horizontal rotation axis 480 (See FIG. 6) of the mobile arm 345 about the collar assembly 170 is aligned perpendicular relative to the central longitudinal axis 500 of the rail support structure 475. The mobile arm 345 and the rail support structure 415 are laterally offset by a distance 505 to one side from the tabletop 490. At this parked position illustrated in FIG. 5, no part of the mobile arm 345 and the rail support structure 415 of the support assembly 340 is aligned in the vertical direction over the tabletop 490 and the imaged subject 310. Accordingly, the ceiling mounted support assembly 340 enhances access and clearance for physician access over the imaged subject 310, and furthermore reduces a likelihood of interference with the above-described laminar flow of air and elevated pressure zone over the table 315 and the imaged subject 310 in a desired manner. As illustrated in FIG. 6, with rotation of the offset arm 440 to a generally perpendicular alignment with the central longitudinal axis 500 of the rail support structure 415 and central longitudinal axis 510 of the tabletop 495, movement of the carriage 410 and/or tabletop 495 in the linear direction 502 allows the isocenter 512 of the imaging system 305 to maintain general continuous alignment with the central longitudinal axis 510 of the tabletop 495 in top plan view, enhancing the ready reference and acquisition of radiological images from the imaged subject 310 while allowing enhanced access to both sides of the imaged subject 310. Referring now to FIG. 7, with rotation of the mobile arm 345 about the second axis 460 with respect to the offset arm 440, movement of the carriage 410 and/or movement of the tabletop 495 in the linear direction 502 allows the isocenter 512 to again maintain general continuous alignment with the central longitudinal axis 510 of the tabletop 495 so as enable the ready capture of radiological images of the subject 310 from head-to-toe, while allowing a clinician or physician enhanced access at the head end and along a right-hand side of the imaged subject 310. In a reverse manner, the imaging system 305 can be readily returned to the parked position illustrated in FIG. 5 from either position illustrated in FIGS. 6 and 7.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An support assembly in movable support of a radiation source and detector operable in combination to acquire a radiological image of a subject positioned on a table, the table having a central longitudinal axis, comprising:
   an offset arm pivotally coupled from a mobile carriage about a first axis generally vertically aligned;
   an elbow pivotally coupled at the offset arm about a second axis generally vertically aligned and spaced an offset distance from the first axis; and
   a mobile arm in support of the radiation source in opposed relation to the radiation detector, the mobile arm pivotally coupled at the elbow about a third axis generally horizontally aligned and in general parallel alignment with the central longitudinal axis of the table in a vertical plane, the mobile arm also supported to rotate about a fourth axis generally horizontal aligned and in general perpendicular alignment relative to the third axis,
   wherein the first axis, the third axis, and the fourth axis all include a common point of intersection with one another,
   wherein the mobile carriage is movable a linear direction along a central longitudinal axis of a fixed rail structure located higher than the table, wherein the central longitudinal axis of the fixed rail structure is generally parallel with the central longitudinal axis of the table and is also spaced an offset distance in a generally horizontal plane from the central longitudinal axis of the table, and wherein no part of the fixed rail structure is aligned above any part of the table in the vertical direction.

2. The assembly of claim 1, further comprising a motorized drive operable to drive rotation of the elbow and mobile arm about the second axis with respect the offset arm.

3. The assembly of claim 1, a motorized drive operable to drive rotation of the offset arm and mobile arm about the first axis with respect to the carriage.

4. The assembly of claim 1, wherein the offset arm includes opposing, generally curvilinear-shaped ends with generally linear sides extending therebetween.

5. The assembly of claim 1, wherein a central longitudinal axis of the offset arm is generally linear aligned between the first and second axes.

6. An arrangement operable to acquire a diagnostic image of a subject, comprising:
   a table to receive the target to be imaged, the table having a central longitudinal axis;
   a carriage operable to move relative to the table;
   an offset arm having a first end opposite a second end, the first end of the offset arm pivotally supported at the carriage about a first axis generally vertically aligned;
   an elbow pivotally supported at the second end of the offset arm about a second axis generally vertically aligned and spaced an offset distance from the first axis;
   a radiation source configured in communication with a radiation detector to acquire the diagnostic image; and
   a mobile arm in support of the radiation source and the radiation detector, the mobile arm pivotally supported from the elbow about a third axis generally horizontally aligned above with the central longitudinal axis of the table in a vertical plane, the mobile arm also slidably supported to rotate about a fourth axis generally horizontal aligned perpendicular relative to the third axis,
   wherein the first axis, the third axis, and the fourth axis all include a common point of intersection with another,
   wherein the carriage is movable along an elevated support structure in a linear direction generally parallel to the central longitudinal axis of the table, wherein a central longitudinal axis of the elevated support structure is spaced an offset distance from the central longitudinal axis of the table in a top plan view, and wherein no part of the elevated support structure is aligned above the table in a vertical direction.

7. The arrangement of claim 6, wherein the radiation source is aligned in communication with respect to the radiation detector along a generally linear, vertical axis that is in general co-alignment with first axis.

8. The arrangement of claim 6, further comprising a motorized drive operable to rotate the elbow and mobile arm about the second axis with respect to the offset arm.

9. The arrangement of claim 6, wherein the imaging system is a radiological imaging system.

10. The arrangement of claim 6, wherein a central longitudinal axis of the offset arm is generally linear aligned between the first and second axes.

11. A method of communicating radiation from a radiation source through a table and to a radiation detector, the method comprising the acts of:

sliding an carriage in a linear direction along a rail fixed and located above in a vertical direction in relation to the table;

pivoting a first end of an offset arm about a first axis with respect to the carriage;

pivoting an elbow about a second end of the offset arm about a second axis generally vertically aligned and spaced an offset distance in a horizontal direction from the first axis;

pivoting a mobile arm about a third axis in relation to the elbow, the third axis being generally horizontally aligned and generally aligned with a central longitudinal axis of the table in a vertical plane; and rotating the mobile arm about a fourth axis in relation to the elbow, the fourth axis generally horizontal aligned and generally perpendicular aligned relative to the third axis; and transmitting radiation from a radiation source at one free end of the mobile arm toward the radiation detector, wherein the act of sliding the carriage in the linear direction is along a longitudinal central axis of the rail aligned generally parallel to, and located at an offset distance in a horizontal direction from, the central longitudinal axis of the table such that no part of the rail and the carriage is aligned above the table in a vertical direction.

* * * * *